(12) United States Patent
Merkt et al.

(10) Patent No.: US 9,839,086 B2
(45) Date of Patent: Dec. 5, 2017

(54) TECHNIQUE FOR ADJUSTING THE BRIGHTNESS OF LED LAMPS

(71) Applicant: HEINE OPTOTECHNIK GMBH & CO KG, Herrsching (DE)

(72) Inventors: Norbert Merkt, Herrsching (DE); Benjamin Komm, Munich (DE); Manfred Wittlinger, Schwabmuenchen (DE); Oliver Heine, Herrsching (DE); Bernd Kabbeck, Landsberg am Lech (DE)

(73) Assignee: HEINE OPTOTECHNIK GMBH & CO KG, Herrsching (DE)

( * ) Notice: Subject to any disclaimer, the term of this patent is extended or adjusted under 35 U.S.C. 154(b) by 0 days.

(21) Appl. No.: 15/164,338

(22) Filed: May 25, 2016

(65) Prior Publication Data

US 2016/0353540 A1 Dec. 1, 2016

(30) Foreign Application Priority Data

May 26, 2015 (DE) .......... 10 2015 108 217

(51) Int. Cl.
*H05B 33/08* (2006.01)
*A61B 1/06* (2006.01)
*A61B 1/227* (2006.01)
*A61B 5/00* (2006.01)

(52) U.S. Cl.
CPC ....... *H05B 33/0848* (2013.01); *A61B 1/0684* (2013.01); *A61B 1/227* (2013.01); *A61B 5/0059* (2013.01); *H05B 33/0854* (2013.01)

(58) Field of Classification Search
CPC ............ H05B 33/0815; H05B 33/0818; H05B 33/0884; H05B 33/0809; H05B 33/0848; H05B 33/0896; H05B 37/0245; H05B 37/0254; H05B 41/3925; H05B 41/391; H05B 41/2828; H05B 33/0803; H05B 37/0272; H05B 33/0857; H05B 33/0887
USPC .......................... 315/182, 186, 307, 291, 24
See application file for complete search history.

(56) References Cited

U.S. PATENT DOCUMENTS 5,851,488 A * 12/1998 Saul ..................... G01N 21/645
                                                          422/67
7,276,025 B2   10/2007 Roberts et al.
7,459,959 B2   12/2008 Rader et al.
(Continued)

FOREIGN PATENT DOCUMENTS

EP          2319391 A1    5/2011

*Primary Examiner* — Douglas W Owens
*Assistant Examiner* — Syed M Kaiser
(74) *Attorney, Agent, or Firm* — Marshall, Gerstein & Borun LLP

(57) ABSTRACT

A method is described for adjusting the brightness of at least one LED according to a changing supply voltage provided to the at least one LED includes acquiring a parameter which indicates the changing supply voltage; and providing, on the basis of the acquired parameter, a control voltage of the at least one LED for adjusting an LED current such that the at least one LED has a predefined relative brightness change over the predefined voltage range. A control unit and an LED lamp which implement the method described here are also discloses. Furthermore, an LED lighting apparatus and a medical diagnostic device having the LED lamp disclosed here are described.

16 Claims, 9 Drawing Sheets

(56) References Cited

U.S. PATENT DOCUMENTS

| | | | |
|---|---|---|---|
| 7,667,408 B2* | 2/2010 | Melanson | H05B 33/0809 315/209 R |
| 8,786,210 B2 | 7/2014 | Delucia | |
| 2004/0252278 A1* | 12/2004 | Williams | A61B 1/0669 351/221 |
| 2007/0045524 A1* | 3/2007 | Rains | F21K 9/00 250/228 |
| 2008/0297069 A1* | 12/2008 | Shao | H05B 33/0815 315/307 |
| 2010/0296285 A1* | 11/2010 | Chemel | F21S 2/005 362/235 |
| 2011/0080110 A1* | 4/2011 | Nuhfer | H05B 33/0815 315/291 |
| 2011/0112378 A1* | 5/2011 | Heine | A61B 1/267 600/249 |
| 2011/0121744 A1* | 5/2011 | Salvestrini | H05B 33/0815 315/246 |
| 2012/0056548 A1 | 3/2012 | Duan et al. | |
| 2012/0074853 A1* | 3/2012 | Weightman | H05B 39/08 315/182 |
| 2013/0188388 A1* | 7/2013 | Jaffe | F21V 9/16 362/580 |
| 2014/0300284 A1* | 10/2014 | Lee | H05B 33/086 315/186 |
| 2015/0133732 A1* | 5/2015 | Goldfain | A61B 1/227 600/200 |
| 2016/0353540 A1* | 12/2016 | Merkt | A61B 1/0684 |

* cited by examiner

TECHNIQUE FOR ADJUSTING THE BRIGHTNESS OF LED LAMPS

FIELD OF THE INVENTION

The present invention relates in general to the field of LED lamps. Specifically, a method and a control unit for adjusting the brightness of at least one LED lamp are described. An LED lamp which comprises such a control unit is also described.

BACKGROUND

Light-emitting diodes, or LEDs in short, are gradually taking over all areas of everyday life. Lighting systems, for example streetlights, vehicle lights, or interior lights, which were equipped in the past with conventional incandescent lamps, are being replaced by or refitted with LED lamps more and more often. This is also true for lighting systems which are used in (mobile or grid-connected stationary) medical diagnostic devices, for example, microscopes, otoscopes, or endoscopes. Incandescent lamps or subminiature incandescent lamps in medical diagnostic devices are gradually being replaced by LED lamps.

The advantage of LED lamps in relation to conventional incandescent lamps is obvious. For example, an LED lamp only consumes a fraction of the electrical energy which a conventional incandescent lamp consumes to generate a comparable luminous flux (and therefore a comparable brightness). Furthermore, in LED lamps, color, color temperature, and brightness can be adjusted flexibly depending on the activation. The service life of LED lamps is, at tens of thousands to 100,000 hours, higher by one or more orders of magnitude than that of conventional incandescent lamps, in which service lives of 1000 to 2000 hours can be expected. In the field of subminiature incandescent lamps for medical diagnostic devices, service lives of even only 10 to 100 hours are achieved. Furthermore, the developers have a substantially higher amount of free space in the optical and mechanical design of LED lamps than in previous solutions.

Since conventional incandescent lamps represent a simple ohmic consumer having a linear current-voltage characteristic curve, the operation of incandescent lamps is very simple. The incandescent lamp merely has to be electrically coupled to a voltage source. The supply voltage provided by the voltage source causes a current proportional to the applied supply voltage to flow through the incandescent coil of the incandescent lamp, and this current causes the incandescent coil to illuminate. The proportionality between the applied supply voltage and the current is determined by the resistance of the incandescent coil according to Ohm's law. By changing the applied supply voltage, the brightness of the incandescent lamp (i.e. the luminous flux of the incandescent lamp) can be changed. The brightness (or dimming) of incandescent lamps can therefore be adjusted directly via adjustment of the supply voltage.

In contrast, the current-voltage characteristic curve of an LED has a diode characteristic having an exponential curve. Above a certain voltage (LED operating voltage), the LED current rises steeply, while the voltage remains almost unchanged. The brightness of an LED lamp therefore cannot be regulated directly via the provided supply voltage. Rather, LEDs are regulated by adjusting the LED current.

Electronic circuits (so-called LED drivers) are used for adjusting the LED current. Conventional LED drivers are designed to provide an approximately constant LED current for operating the LEDs. Circuits which keep the LED current constant or compensate for a voltage difference between the power supply and LED are known, inter alia, from U.S. Pat. No. 7,276,025 B2, EP 2 319 391 A1, US 2008/297069 A1, and U.S. Pat. No. 7,459,959 B2.

The dimming of an LED lamp can be achieved, for example, by changing the LED current. LED drivers, which in comparison to conventional LED drivers have an additional control channel having an external control input to which a control voltage is applied for adjusting the LED current, are also known from the prior art. In most cases, an additional analog signal (for example, 0-10 V) or a signal having pulse width modulation (PWM) is applied to the control terminal of the driver. Control options via the feedback path of LED drivers are also known.

An LED circuit is known from U.S. Pat. No. 8,786,210 B2, in which the LED is electrically coupled directly to the supply voltage input of the LED driver via a measurement resistor having a voltage output of an LED driver and via two further resistors, which function as voltage dividers. The resistors functioning as the voltage dividers have the effect that the potential difference (voltage) applied to the measurement resistor can be changed according to the supply voltage. Since the LED driver adjusts the LED current according to the potential difference, the LED current (and therefore the brightness of the LED) can be adjusted by changing the supply voltage.

In mobile and stationary diagnostic devices, light microscopes and instrument lights, lighting systems are generally used, which enable dimming of the incandescent lamp over a predefined brightness range. Either electronically variable voltage sources or fixed voltage sources (for example, accumulator cells), which are electrically coupled to an adjustable electrical resistor (for example, a rheostat), are used for dimming the incandescent lamp in the lighting systems. The adjustable electrical resistor is arranged in series with the incandescent lamp in the electrical circuit. Because of its serial arrangement, the adjustable resistor is also referred to hereafter as an adjustable series resistor. It functions as an adjustable series resistor for the continuous adjustment of the supply voltage for the incandescent lamp. If the resistance value at the adjustable resistor is increased, the supply voltage applied at the incandescent lamp decreases and vice versa. The brightness of the incandescent lamp increases or decreases accordingly. In other words, the adjustable series resistor functions as a brightness regulator.

This simple regulating mechanism no longer functions if the incandescent lamp of a lighting apparatus is replaced by an LED lamp having a separate LED driver. The reason for this is that LED lamps have a substantially higher resistance than incandescent lamps having equal or similar luminous flux. Therefore, the voltage division ratio specified by the series resistance and the resistance of the LED lamp changes such that a change in the series resistance only causes a slight change in the supply voltage. Therefore, even if an LED driver having an external control unit is used for the voltage-dependent control of the LED current, only slight, hardly perceptible dimming can be achieved. In particular, the fine adjusting in the lower brightness range, which is important for medical applications, is lost.

The use of a rheostat, which is designed for adjusting higher resistance values, could technically solve the problem, but would have the result that, upon the replacement of the incandescent lamp by an LED lamp, the provided electrical supply apparatuses having a fixed voltage source and a rheostat would also have to be completely replaced. In medical diagnostic devices, the fixed voltage source and rheostat are generally integrated in the instrument handle.

Such instrument handles are used in the millions worldwide. The replacement of the instrument handles would cause very high costs and would be logistically very complex, which is not economically acceptable.

SUMMARY

It is therefore the object of the present invention to provide a method and a control unit for adjusting the brightness of an LED lamp, which enables the continued use of voltage sources already in use that have brightness regulators and are designed for the dimming of conventional incandescent lamps.

According to a first aspect of the present disclosure, a method is provided for adjusting the brightness of at least one LED according to a changing supply voltage which is provided to the at least one LED, wherein the supply voltage is provided by means of an electrical supply apparatus, which is designed for providing supply voltages over a predefined voltage range, to adjust the brightness of an incandescent lamp. The method is carried out by means of a control unit, which is provided for electrically coupling the electrical supply apparatus to the at least one LED, and comprises the following steps: acquiring a parameter which indicates the changing supply voltage of the supply apparatus; and providing, on the basis of the acquired parameter, a control voltage of the at least one LED for adjusting an LED current such that the at least one LED has a predefined relative brightness change over the predefined voltage range.

The at least one LED can be designed for generating a white light. It can have a comparable brightness to the incandescent lamp to be replaced by the at least one LED.

The electrical supply apparatus can be designed as an electronically variable voltage source or fixed voltage source (comprising one or more accumulator cells or batteries). If the supply apparatus is designed as a fixed voltage source which outputs a constant voltage value, the supply apparatus can thus additionally comprise an adjustable electrical series resistor (for example, a rheostat), which is designed to supply a lamp with various supply voltages within a predefined voltage range. By adjusting (actuating) the adjustable series resistor, the electrical power supplied to the lamp (and therefore the brightness of the lamp) can thus be regulated.

The voltage range provided by the supply apparatus for adjusting the brightness can be defined by a maximum supply voltage (supply voltage value) and a minimum supply voltage (supply voltage value) provided by the supply apparatus. The maximum supply voltage provided by the supply apparatus can be selected in this case such that an incandescent lamp reaches its maximum brightness (without destroying the incandescent lamp) upon application of the maximum supply voltage. Starting from the maximum supply voltage, by changing the provided supply voltage toward the minimum supply voltage, the brightness of the incandescent lamp can thus be continuously reduced. The minimum supply voltage can be selected in this case such that upon application of the minimum supply voltage, the incandescent lamp has a substantially imperceptible brightness. According to one variant, the minimum supply voltage can assume the value 0 V or a small voltage value (for example, 1 V or 2 V) different from 0 V.

Hereafter, brightness change can mean a change in the brightness (or a variable which describes the brightness of an incandescent lamp or an LED, for example the electrical power consumed by the incandescent lamp or the at least one LED or the luminous flux generated by the at least one LED or incandescent lamp) according to a supply voltage change. In other words, brightness change can mean an increase/decrease of the brightness according to a predefined increase/decrease of the supply voltage in the predefined voltage range. Relative brightness change can mean the brightness change in the at least one LED or the incandescent lamp in each case in relation to its maximum brightness. In other words, the relative brightness change can describe the relative decrease/increase of the brightness of the at least one LED or incandescent lamp in relation to the maximum brightness of the LED or incandescent lamp. The maximum brightness of the at least one LED and the incandescent lamp can be achieved upon the provision of the maximum supply voltage.

The brightness change in the at least one LED and the incandescent lamp over the provided voltage range can be described in each case by a brightness-voltage characteristic curve. This can describe the curve of a parameter which describes the brightness, for example the electrical power consumed in each case by the at least one LED and the incandescent lamp or the luminous flux generated in each case by the at least one LED and the incandescent lamp, according to the supply voltages provided by the supply apparatus (within the provided voltage range). In the same way, relative brightness change in the at least one LED and the incandescent lamp can each be described by a normalized brightness-voltage characteristic curve. The normalized brightness-voltage characteristic curves for the at least one LED and the incandescent lamp can be obtained by normalizing the brightness-voltage characteristic curves with respect to the respective maximum brightnesses of the LED and the incandescent lamp. The control voltage can be provided on the basis of the acquired parameter, which refers to the provided supply voltage, such that a normalized brightness-voltage characteristic curve, which describes the relative brightness change, of the at least one LED is (substantially) identical or similar to a normalized brightness-voltage characteristic curve of an incandescent lamp over the predefined voltage range.

According to one alternative variant, the control voltage can also be provided on the basis of the acquired parameter, which indicates the provided supply voltage, such that the at least one LED follows a normalized brightness-voltage characteristic curve, which deviates from an incandescent lamp characteristic curve, over the predefined voltage range. By way of targeted adjustment (scaling) of the control voltage, the at least one LED can therefore be dimmable in accordance with an arbitrarily pre-definable brightness-voltage characteristic curve over the predefined voltage range.

The step of providing a control voltage can comprise a calculation of the control voltage on the basis of the acquired parameter and at least one pre-definable dimming characteristic curve. The at least one dimming characteristic curve can describe, for the predefined voltage range, a predefined functional dependence of the control voltage on the acquired parameter. The functional dependence of the control voltage on the acquired parameter can be described, for example, by means of a predefined power function or a logarithmic function. According to one variant, the dimming characteristic curve can describe a quadratic dependence of the control voltage on the acquired parameters. The quadratic dependence can be described in this case by a single quadratic characteristic curve. Alternatively, the quadratic dependence of the control voltage or the dependence of the control voltage according to a predefined power or logarithmic function can also be approximated by multiple linear characteristic curves over the predefined voltage range. The quadratic dependence of the control voltage on the acquired parameter can cause the LED current adjusted by the control voltage to change substantially as the square of the provided supply voltage. In this manner, it is possible to simulate the brightness curve of an incandescent lamp, which has a quadratic dependence on the provided supply voltage.

The step of acquiring a parameter can comprise the following substeps: coupling an electrical load resistor, which simulates an electrical resistance of the incandescent lamp, to the supply apparatus; and acquiring the parameter by measuring the voltage which drops at the load resistor. The load resistor which simulates the incandescent lamp can have a resistance value in this case which corresponds to the resistance value of the incandescent lamp during operation. If the supply apparatus is designed as a fixed voltage source which comprises an adjustable series resistor for adjusting a supply voltage, coupling of the load resistor to the electrical supply apparatus can result in a serial arrangement of the load resistor and adjustable series resistor. The load resistor and adjustable series resistor can implement a voltage divider, wherein the voltage component (partial voltage) which drops over the load resistor in relation to the voltage provided by the fixed voltage source is dependent on the resistance ratio of load resistor and the total resistance generated by load resistor and adjustable series resistor. Since the load resistor simulates the resistance of the incandescent lamp in the circuit, the voltage acquired at the load resistor can correspond to the supply voltage which would be applied to the incandescent lamp if the incandescent lamp were directly electrically coupled to the fixed voltage source. In contrast, if the supply apparatus is implemented as an electronically variable voltage source, the supply voltage provided by the voltage source can thus also be acquired by means of the load resistor. Independently of the embodiment of the supply apparatus, the supply voltage provided by the supply apparatus can be directly acquired at any time by means of the load resistor. Alternatively, instead of the voltage acquired by means of the load resistor, another measured variable, for example the actuation of the adjustable series resistor (for example, direct acquisition of the rheostat angle), can also be acquired as the parameter.

The step of electrically coupling the load resistor can comprise selective coupling and decoupling of the load resistor to and from the electrical supply apparatus. The load resistor can be coupled to the electrical supply apparatus for a predefined duration for this purpose. During this time, the voltage which drops at the coupled load resistor can then be ascertained. The coupling duration can be restricted in this case to a few microseconds. This short duration can be sufficient to measure the voltage which drops at the load resistor. A restriction of the coupling to a predefined short duration can be advantageous to keep dissipative losses low, as occur at the load resistor upon coupling of the load resistor. Alternatively, the load resistor can be permanently coupled to the electrical supply apparatus.

The steps of acquiring a parameter and providing a control voltage can be repeated at chronologically successive intervals. According to one implementation, the steps of acquiring a parameter and providing a control voltage can be repeated at a predefined frequency. For example, the predefined frequency can assume a value in the range of 10 Hz to 10 000 Hz, preferably a value in the range of 100 Hz to 10 000 Hz. Due to the high repetition rate, changes in the provided supply voltage can be acquired without significant time delay and control voltages adapted to the changed supply voltages can be provided. In this manner, substantially simultaneous adaptation of the brightness of the at least one LED to a change in the supply voltage is enabled by the method.

According to a further aspect, a control unit is provided for adjusting the brightness of at least one LED according to a changing supply voltage which is provided to the at least one LED, wherein the control unit is designed for electrically coupling the at least one LED to an electrical supply apparatus, which is designed to provide supply voltages over a predefined voltage range, in order to adjust the brightness of an incandescent lamp. The control unit comprises an acquisition apparatus, which is designed to acquire a parameter which indicates the changing supply voltage; and a provision apparatus, which is designed to provide, on the basis of the acquired parameter, a control voltage of the at least one LED for adjusting an LED current such that the at least one LED has a predefined relative brightness change over the predefined voltage range.

The provision apparatus can be designed to calculate the control voltage on the basis of the acquired parameter and at least one predefined dimming characteristic curve. For example, the at least one dimming characteristic curve for the predefined voltage range can describe a dependence of the control voltage on the acquired parameter according to a predefined power function or logarithmic function. According to one variant, the dimming characteristic curve can have a quadratic dependence of the control voltage on the acquired parameter. Both the quadratic dimming characteristic curve and also the dimming characteristic curves according to a predefined power or logarithmic function can each be described by a corresponding single characteristic curve or by multiple linear characteristic curves which approximate the corresponding characteristic curves.

The at least one dimming characteristic curve can be stored in the provision apparatus. It can be implemented as an analog circuit or in the form of a digital assignment table (lookup table) in the provision apparatus.

The control unit can furthermore comprise an electrical load resistor, which simulates an electrical resistance of an incandescent lamp and is provided for electrical coupling to the electrical supply apparatus. In this case, the load resistor which simulates the incandescent lamp can have a resistance value which corresponds to the resistance value of the incandescent lamp during operation. In this manner, the control unit can simulate the circuit of the incandescent lamp. By coupling the electrical load resistor to the electrical supply apparatus, the voltage which drops at the load resistor can be acquired by means of the acquisition apparatus. The voltage which drops at the load resistor can correspond in this case to the supply voltage provided to the incandescent lamp.

The control unit can furthermore comprise a switching apparatus, which is designed to implement at least two switching states. The switching apparatus can be designed for the purpose of electrically coupling the load resistor of the control unit to the electrical supply apparatus in a first switching state. The switching apparatus can furthermore be designed for the purpose of electrically coupling the electrical supply apparatus to the at least one LED (or to the LED driver) in a second switching state, in order to power the at least one LED or the LED driver. At the same time, in the second switching state, the load resistor can be decoupled from the electrical supply apparatus. The load resistor can be completely electrically decoupled from the circuit of the LED driver by the switching apparatus. This has the advantage that the partial voltage which drops at the load resistor is not influenced by the circuit of the LED driver, whereby the acquisition of the voltage which drops at the load resistor can be improved. Furthermore, by means of the switching apparatus, the coupling of the load resistor to the voltage source can be limited to a minimum time required for the measurement of the partial voltage, whereby dissipative power losses at the loaded load resistor are kept as low as possible. According to an alternative variant, the at least one LED or the LED driver can be (or remain) electrically coupled to the electrical supply apparatus independently of the switching state of the switching apparatus (i.e. also in the first switching state). In this case, in the first switching state, the at least one LED or the LED driver would, together with a proportional load resistor, simulate the circuit of the incandescent lamp.

The control unit can furthermore comprise a clock generator apparatus, which is electrically coupled to the switching apparatus, for activating the switching apparatus.

The clock generator apparatus is designed to generate an electrical pulse sequence, to switch the switching apparatus back-and-forth between the at least two switching states. The generated pulse sequence can be chronologically successive voltage pulses or current pulses. These pulses can be generated at a fixed (preset or pre-settable) frequency by the clock generator apparatus.

The clock generator apparatus can be designed to generate pulses at a predefined frequency. For example, the predefined frequency can assume a value in the range between 10 Hz and 10 000 Hz, preferably a value in the range between 100 Hz and 10 000 Hz. The switching apparatus can then be switched back-and-forth between the two switching states at the predefined frequency of the pulse sequence. The acquisition of the voltage component which drops over the load resistor can therefore be chronologically repeated at the frequency of the pulse sequence. The acquisition of the series resistance can be repeated multiple times per second due to the high clock frequencies. The acquisition can therefore be performed practically continuously. It is therefore ensured that changes in the series resistance, and accompanying changes in the voltage which drops over the load resistor, can be acquired immediately (i.e. without substantial time delay) and converted into corresponding control voltages for the LED driver. Very rapid adaptation of the LED brightness to a changed series resistance value is thus enabled by the control unit.

The time for which the switching apparatus remains in the first switching state, and therefore couples the load resistor to the series resistor and the voltage supply, can be established by a pre-settable pulse duration. In general, the duration can be restricted to a few microseconds, to enable reliable acquisition of the voltage applied at the load resistor. Accordingly, the clock generator apparatus can be designed such that it generates pulses having a pulse duration of a few microseconds (for example, pulse durations in the range between 1 μs and 10 μs). The short dwell time of the switching apparatus in the first switching state has no effect on the electrical supply of the LED, which is briefly interrupted by the switching into the first switching state. This is because LED drivers generally have buffer capacitors for storing electrical energy, which can easily bridge the short supply interruption.

The clock generator apparatus can furthermore be electrically coupled to the acquisition apparatus, to provide the generated pulse sequence to the acquisition apparatus. In this manner, the acquisition of the voltage applied at the load resistor can be synchronized with the coupling of the load resistor to the voltage source and the series resistor. According to one variant, the acquisition of the voltage at the load resistor can be performed with a slight time delay to the switching over into the first switching state. This prevents settling effects, which occur upon switching over, from corrupting the acquisition.

The control unit can be designed as a hardware module and/or a software module. According to one variant, the control unit can be designed as an analog unit having an analog acquisition apparatus and provision apparatus. The provision apparatus can comprise an analog circuit, which converts the acquired parameter into a corresponding control signal according to the characteristic of the above-mentioned at least one dimming characteristic curve. In this case, the acquisition apparatus and provision apparatus can each be designed as separate units which are electrically coupled to one another. Alternatively, the acquisition apparatus and the provision apparatus can be designed as one electronic unit.

Alternatively, the control unit can also be implemented as a microcontroller having at least one processor (and at least one memory). In this case, the dimming characteristic curve can be stored in the form of an assignment table (lookup table) in the microcontroller. The control unit can furthermore comprise an analog-to-digital converter, which converts the voltage signal tapped at the load resistor into a corresponding digital signal sequence, as well as a digital-to-analog converter, which converts the provided control voltage signal into a corresponding analog signal for the LED driver.

According to a further aspect, an LED lamp is provided, which is designed for electrical coupling to an electrical supply apparatus, wherein the electrical supply apparatus is designed to provide supply voltages over a predefined voltage range, in order to adjust the brightness of an incandescent lamp. The LED lamp comprises the above-described control unit for providing a control voltage on the basis of the supply voltage provided by the supply apparatus; an LED driver, which is electrically coupled to the control unit and is designed to generate an LED current for the at least one LED on the basis of the provided control voltage; and at least one LED, which is electrically coupled to the LED driver, for generating a luminous flux on the basis of the provided LED current.

The LED lamp can be provided for use in medical diagnostic devices (for example, otoscopes, endoscopes). The LED lamp can be designed as an independent unit, which is compatible with electrical supply apparatuses installed in medical diagnostic devices (for example, supply apparatuses having a fixed voltage source and an adjustable series resistor). The LED lamp can furthermore comprise two electrical terminals (one terminal for the phase and one terminal for the ground), via which the LED lamp is electrically connectable to the voltage sources installed in medical diagnostic devices.

The at least one LED can be designed to generate a white light. The LED driver can accordingly be designed to generate an LED current for the at least one white LED lamp. Any commercially available LED driver having an external control input for the voltage-dependent adjustment of the LED current can be used as the LED driver, as described at the outset. The external control input is electrically coupled to the control unit. The control signal provided by the provision apparatus can therefore be supplied to the external control input. According to one variant, the LED driver can also be integrated in the control unit.

According to a further aspect, an LED lighting apparatus is provided, which comprises the above-described LED lamp and an electrical supply apparatus coupled to the LED lamp, wherein the electrical supply apparatus is designed to provide the supply voltages over a predefined voltage range, to continuously adjust the brightness of an incandescent lamp.

The electrical supply apparatus can be designed as an electronically variable voltage source or as a fixed voltage source (comprising one or more accumulator cells or batteries), which is coupled to an adjustable series resistor for adjusting the lamp brightness, as described above.

According to a further aspect, a medical diagnostic device is provided, comprising the LED lighting apparatus described here. The medical diagnostic device can be designed in the form of an otoscope, an endoscope, or a microscope.

Further aspects, advantages, and details of the present invention result from the following description of the exemplary embodiments in conjunction with the figures. In the figures:

DETAILED DESCRIPTION

Figure 1:
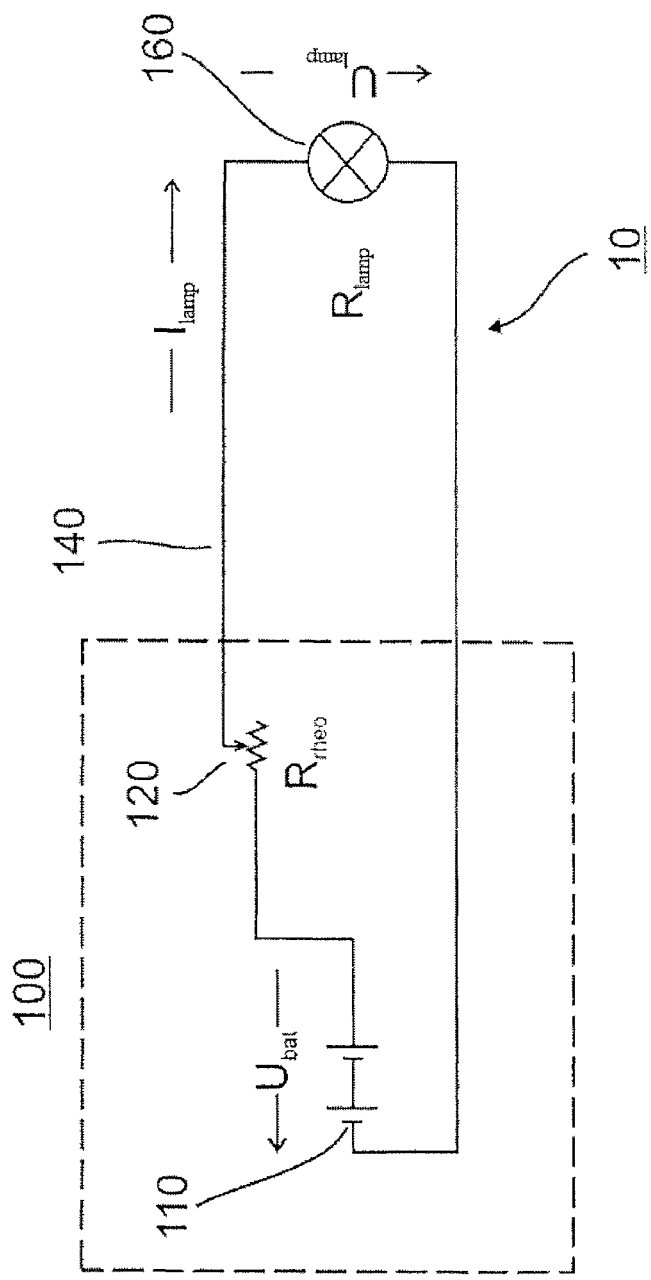
FIG. 1 shows an electric circuit of a lighting apparatus having an incandescent lamp according to the prior art.

FIG. 1 shows, on the basis of a circuit diagram, an electrical circuit of a lighting apparatus 10, as is used, for example, in medical diagnostic devices. The lighting apparatus 10 comprises an electrical supply apparatus 100 and an incandescent lamp 160, which is electrically connected to the supply apparatus 100. The supply apparatus 100 comprises a voltage source 110 (generally a battery, which provides a predefined fixed voltage) and a rheostat 120 arranged in the electrical circuit 140. The supply apparatus 100 can be designed as an independent subunit of the lighting apparatus 10 that is installed separately in a medical diagnostic device, for example (shown in FIG. 1 by the dashed line).

The rheostat 120 represents an adjustable series resistor, which is used for the continuous adjustment of the brightness (dimming) of the incandescent lamp 160. By actuating the rheostat 120, the series resistance value $R_{rheo}$ changes and the following relation applies for the voltage (or partial voltage) $U_{lamp}$ applied to the incandescent lamp 160:

$$U_{lamp}=U_{bat}*R_{lamp}/(R_{rheo}+R_{lamp}), \quad (1)$$

wherein $U_{bat}$ designates the voltage provided by the voltage source 110 (battery), $R_{lamp}$ designates the resistance of the incandescent lamp 160, and $R_{rheo}$ designates the variable resistance of the rheostat 120.

It should be noted that the luminous flux generated by the incandescent lamp 160 (or equivalently the brightness of the incandescent lamp) is directly proportional to the consumed electrical power. Changes in the electrical power cause corresponding changes in the brightness of the incandescent lamp 160. Therefore, for the further considerations, the electrical power consumed by the incandescent lamp 160 will be used to describe the brightness.

Since the incandescent lamp 160 represents an ohmic consumer, the electrical power consumed at the incandescent lamp 160 can be calculated according to the equation $$P_{lamp}=U_{lamp}*I_{lamp}=U_{lamp}^2/R_{lamp}=(U_{bat}*R_{lamp}/(R_{rheo}+R_{lamp}))^2/R_{lamp} \quad (2)$$

Equation (2) shows that the electrical power of the incandescent lamp 160 is a function of the square of the partial voltage $U_{lamp}$ which drops over the incandescent lamp 160. The partial voltage $U_{lamp}$ which drops over the incandescent lamp 160 is in turn a function of the ratio of internal resistance of the incandescent lamp $R_{lamp}$ to total resistance ($R_{rheo}+R_{lamp}$), wherein the total resistance is variably changeable based on the rheostat setting.

For example, if the value $R_{rheo}=0$, the maximum voltage provided by the voltage source 110 is thus applied to the incandescent lamp 160, whereby a maximum lamp power $$P_{lamp\ max}=U_{bat}^2/R_{lamp} \quad (2a)$$

and therefore a maximum brightness of the incandescent lamp 160 results. In contrast, if the rheostat assumes the value $R_{rheo}=R_{lamp}$ at full deflection (in the following example, it is assumed that this is reached at a 90° deflection), the lamp power would thus be reduced to $$P_{lamp}=U_{bat}^2/(4*R_{lamp})=P_{lamp\ max}/4 \quad (2b)$$

Figure 7A:
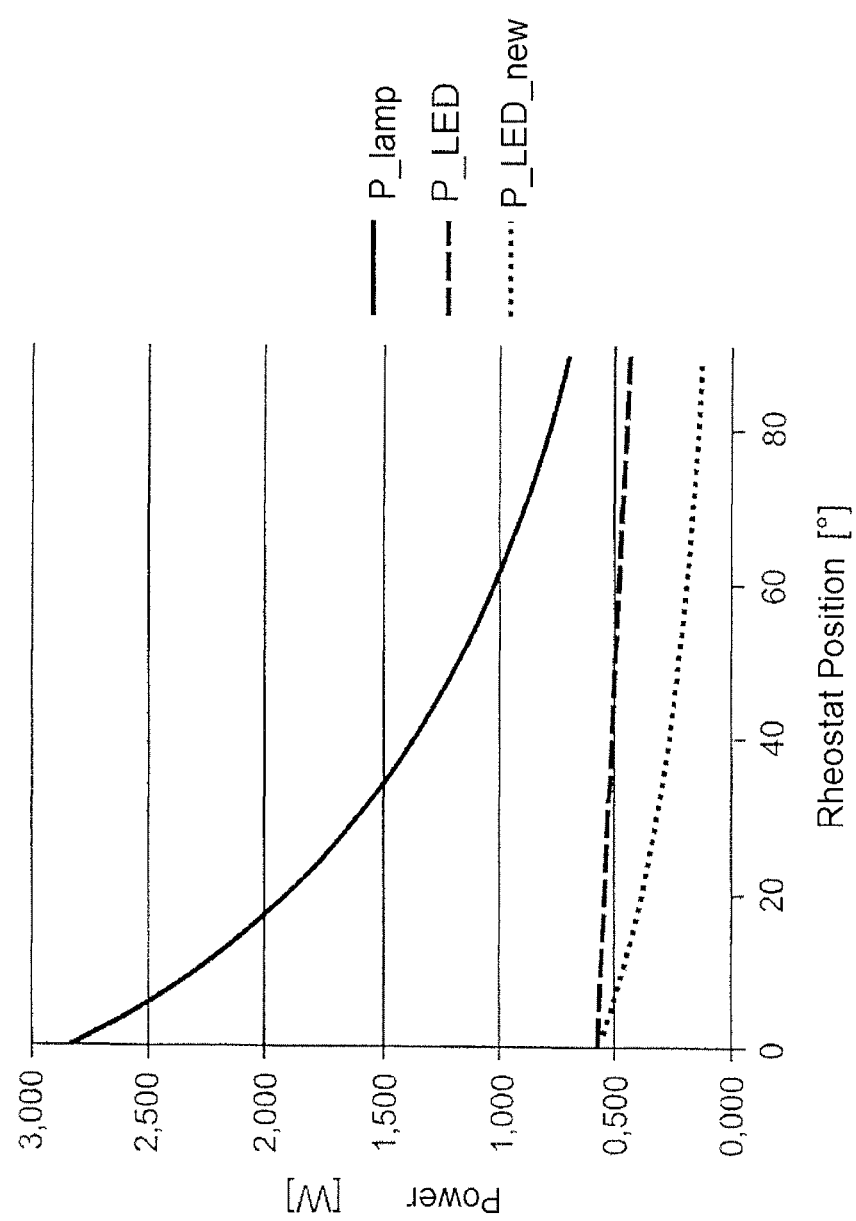
FIGS. 7A and 7B show two diagrams, which illustrate the brightness change in an LED lamp and an incandescent lamp on the basis of a rheostat setting.
Figure 7B:
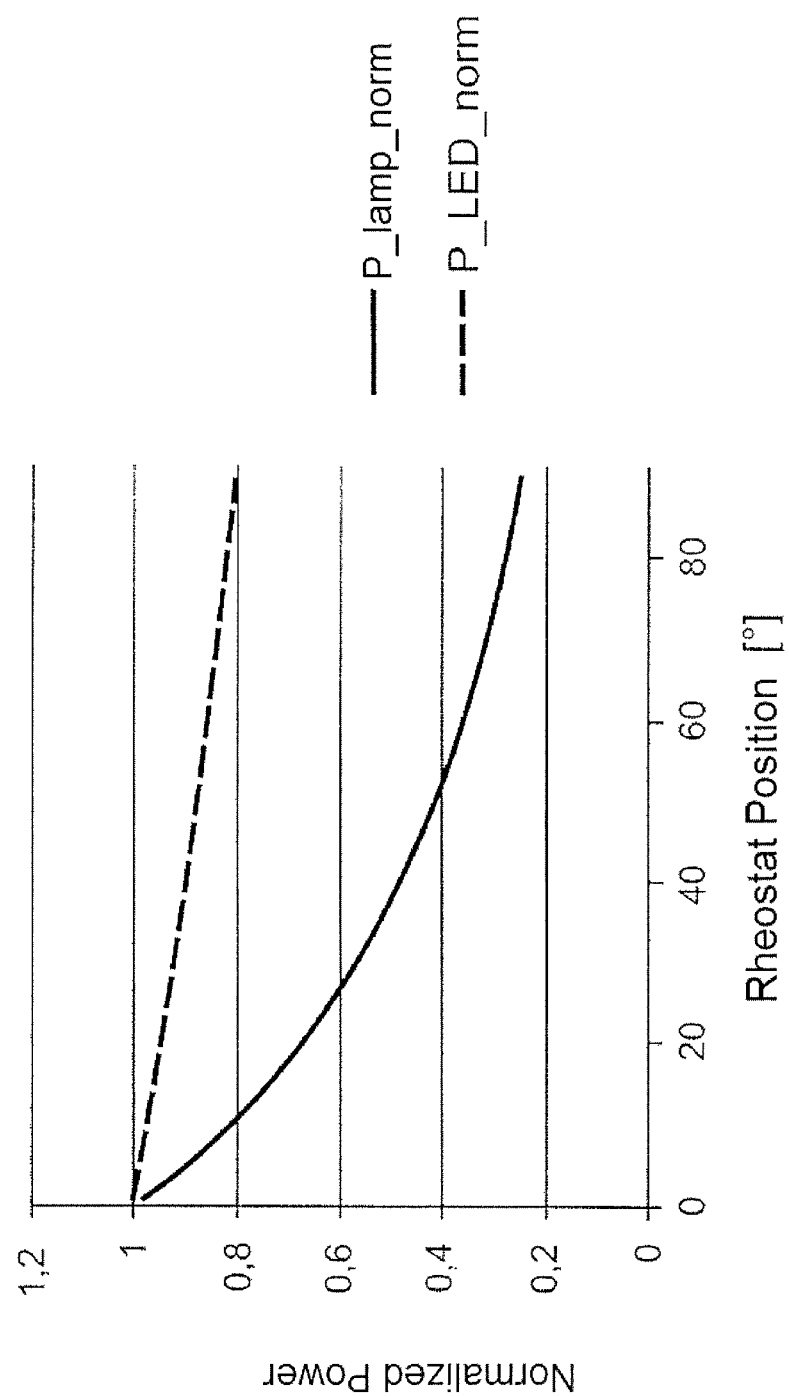

In other words, the electrical power consumed at the incandescent lamp 160 would drop to 25% of the maximum lamp power $P_{lamp\ max}$. Accordingly, the brightness of the incandescent lamp 160 can be dimmed by the rheostat 120 to 25% of the maximum incandescent lamp brightness. In the example discussed here, the electrical power and therefore the brightness can be adjusted variably between 100% and 25% using the rheostat 120. The dimming characteristic of the incandescent lamp 160 is illustrated by the brightness-voltage characteristic curves "P_lamp" and "P_lamp_norm" shown in FIGS. 7A and 7B. Specifically, in FIG. 7A, the electrical power (this is a measure of the brightness of the incandescent lamp 160) is plotted as a function of the rheostat deflection (this is a measure of the voltage applied to the incandescent lamp). The characteristic curve shows the quadratic dependence described in equation (2) of the power (brightness) of the incandescent lamp 160 on the supply voltage $U_{lamp}$. In FIG. 7B the characteristic curve "P_lamp" shown in FIG. 7A is plotted in a manner normalized to the maximum power (brightness) for better comparability. It goes without saying that lower lamp powers can also be achieved with a higher resistance value of the rheostat 120 ($R_{rheo}>>R_{lamp}$). The example described here is used solely for illustration of how the electrical power changes according to the rheostat setting.

Figure 2A:
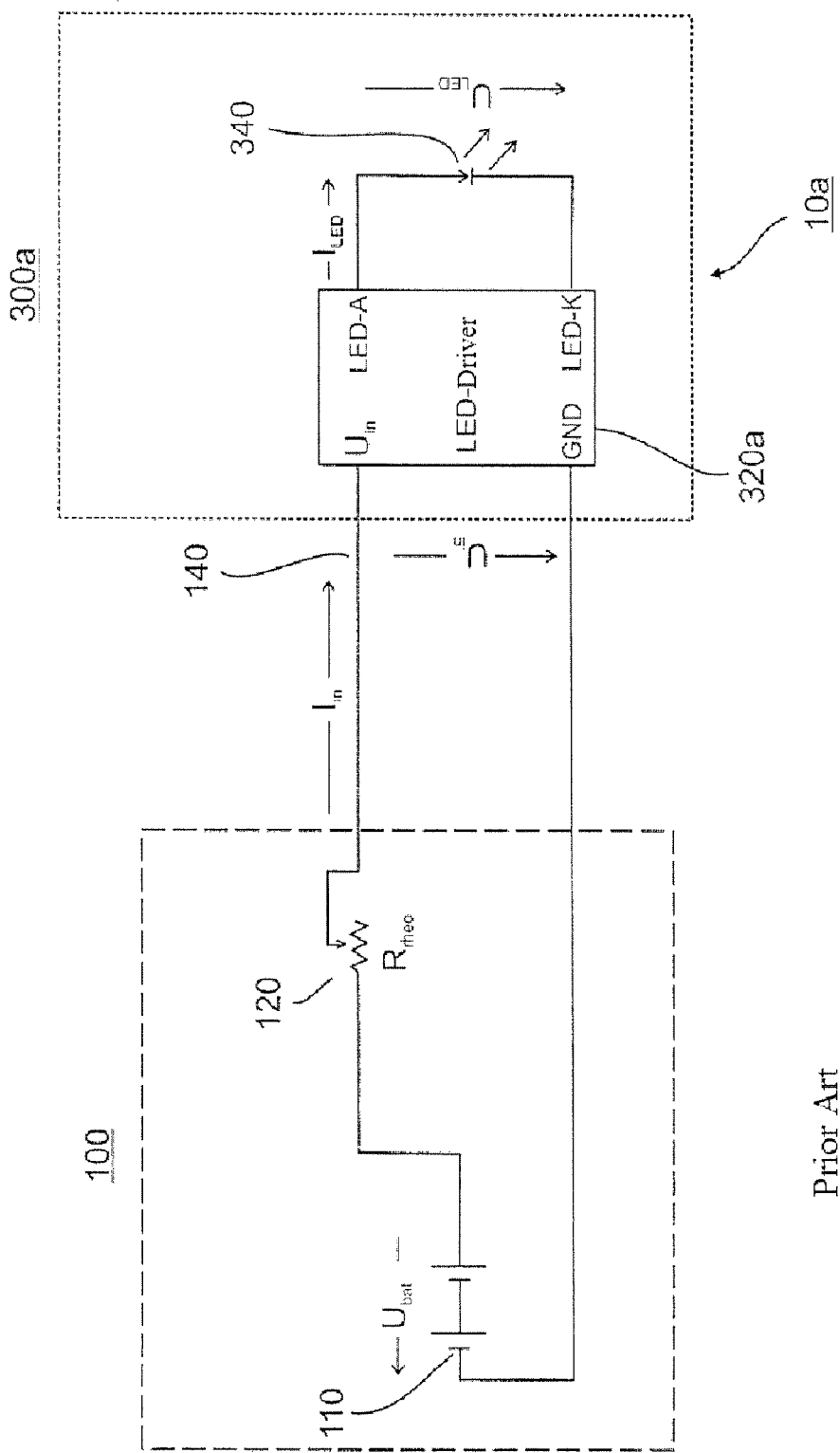
FIGS. 2A and 2B show an electric circuit of a lighting apparatus having an LED lamp with and without brightness adjustment according to the prior art.

A lighting apparatus 10a will now be described in conjunction with FIG. 2A, in which an LED lamp 300a is used instead of the incandescent lamp 160 shown in FIG. 1. The LED lamp 300a comprises an LED 340 and a conventional LED driver 320a, which is electrically connected to the LED 340. This driver is designed to output a constant current to the LED 340 for activating the LED 340. The input of the LED driver 320a is in turn electrically coupled to the supply apparatus 100 discussed in conjunction with FIG. 1.

If the input voltage ($U_{in}$) is changed via the rheostat 120, the LED current $I_{LED}$ does not change. In other words, the rheostat 120 has no effect in the LED lamp 300a having the LED driver 320a. The following equations apply here:

$$P_{LED} = U_{LED} * I_{LED} = \eta * U_{in} * I_{in}, \qquad (3)$$

wherein $P_{LED}$ is the electrical power of the LED 340 and $\eta$ is the efficiency of the LED driver 320a. In equation (3), generally $\eta < 1$. This means that the electrical power consumed by the LED driver 320a ($P_{in} = U_{in} * I_{in}$) is greater than the power provided to the LED 340. $U_{LED}$ is nearly constant as a physical condition. $I_{LED}$ is kept constant by the LED driver 320a. That is to say, when $U_{in}$ becomes smaller, $I_{in}$ becomes greater and vice versa. The LED lamp 300a shown in FIG. 2A is not dimmable.

Figure 2B:
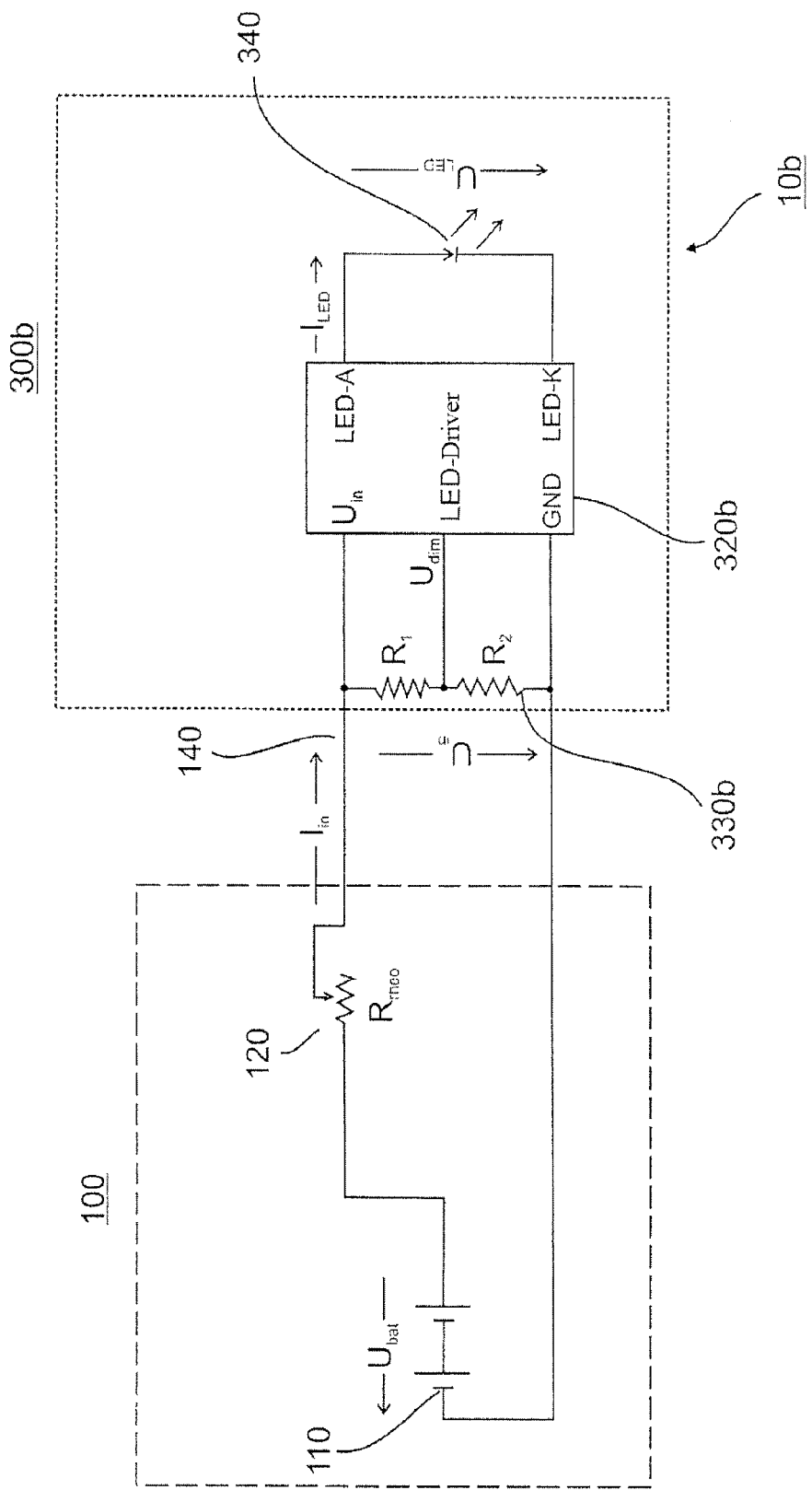

A lighting apparatus 10b having a dimmable LED lamp 300b will be described in greater detail on the basis of FIG. 2B. FIG. 2B shows an LED lamp 300b, which is again electrically coupled to the electrical supply device 100 described in conjunction with FIG. 1. The difference from the LED lamp 300a shown in FIG. 2A is that a "dimmable" LED driver 320b is provided. This driver is provided with an additional control input. A control voltage $U_{dim}$ for dimming the LED 340 can be applied to the control input and can be tapped at a voltage divider 330b arranged in parallel with the LED driver 320b. Such LED drivers are generally available on the market and the following relations apply:

$$I_{LED} = I_{LED\ max} * (U_{dim}/U_{dim\ max}) \text{ and} \qquad (4a)$$

$$U_{dim}/U_{dim\ max} = U_{in}/U_{in\ max}, \qquad (4b)$$

wherein $I_{LED\ max}$ designates a maximum LED current, $U_{dim\ max}$ describes a maximum control voltage, $U_{in\ max}$ designates a maximum input voltage, and $U_{in}$ designates the set input voltage.

The maximum control voltage $U_{dim\ max}$ is reached when the rheostat 120 assumes the value zero, i.e. when the following equation applies $$U_{in\ max} = U_{bat} \text{ (when } R_{rheo} = 0 \text{)}. \qquad (4c)$$

In this case $U_{dim} = U_{dim\ max}$ and $I_{LED} = I_{LED\ max}$ apply, as can be derived immediately when equations (4a-4c) are considered together.

Since the LED lamp 300b only consumes a fraction of the electrical energy of the incandescent lamp 160 to generate the same luminous flux (the same quantity of light), the following relations furthermore apply:

$$P_{LED\ max} = v_e * P_{lamp\ max}, \text{ or} \qquad (5a)$$

$$P_{LED} = v_e * P_{lamp}, \text{ with } v_e < 1, \qquad (5b)$$

wherein $P_{lamp}$ and $P_{lamp\ max}$ designate the (maximum) power of the incandescent lamp 160 and $P_{LED}$ and $P_{LED\ max}$ designate the (maximum) power of the LED 340. $v_e$ designates a proportionality factor, which assumes values between 0.16 and 0.2 in current LEDs having high-quality light.

A so-called virtual resistance of the LED lamp 300b (LED 340 and LED driver 320b together) can now be estimated with the aid of the equations (4a-5b), and is defined by the relation $$R_{LED\ virt} = U_{in}/I_{in} \qquad (6)$$

Similarly to equation (2) above, the following equation applies for the circuit in FIG. 2B having the rheostat 120 arranged in the circuit 140

$$U_{in} = U_{bat} * (R_{LED\ virt}/(R_{rheo} + R_{LED\ virt})). \qquad (7)$$

By rearranging equations (3) and (5b), the following may also be written $$I_{in} = P_{LED}/(\eta * U_{in}) \text{ and } I_{in} = (v_e * P_{lamp})/(\eta * U_{in}) \qquad (8)$$

Equation (8) inserted into equation (6) results in $$R_{LED\ virt} = U_{in}/((v_e * P_{lamp})/(\eta * U_{in})) = \eta * U_{in}^2 / (v_e * P_{lamp}) = (\eta/v_e) * R_{lamp}. \qquad (9)$$

By inserting common values for $\eta = 0.8$ and $v_e = 0.2$, a value can be estimated for the virtual resistance $R_{LED\ virt} = 4 * R_{lamp}$. In other words, the resistance of the LED lamp 300b is higher by a factor of 4 than the resistance at the incandescent lamp 160, which generates a similar luminous flux to the LED lamp.

As a result of the much higher resistance of the LED lamp 300b, a rheostat 120 provided for regulating the brightness of an incandescent lamp having similar luminous flux is not suitable for performing a similar brightness adjustment on the LED lamp 300b. This will be illustrated further on the basis of the example described here.

By means of equation (9), equation (7) can be converted into the equation $$U_{in} = U_{bat} * (((\eta/v_e) * R_{lamp})/(R_{rheo} + ((\eta/v_e) * R_{lamp}))) \qquad (10)$$

If $R_{rheo} = 0$, then $U_{in} = U_{bat}$ and the following equations apply:

$$I_{in} = I_{in\ max} = v_e * P_{lamp\ max}/(\eta * U_{bat}) = (v_e/\eta) * (P_{lamp\ max}/U_{bat}) \text{ and} \qquad (11a)$$

$$I_{in\ max} = (v_e/\eta) * I_{lamp\ max}. \qquad (11b)$$

If the rheostat 120 is adjusted to the value $R_{lamp}$ at full deflection (90° deflection as in the circuit in FIG. 1), the following equation furthermore applies:

$$U_{in} = U_{bat} * (((\eta/v_e) * R_{lamp})/(R_{lamp} + (\eta/v_e) * R_{lamp}))) = U_{bat} * 1/((v_e/\eta) + 1). \qquad (12)$$

At values of $\eta = 0.8$ and $v_e = 0.2$, an input voltage as follows results therefrom $$U_{in} = U_{bat} * 0.8 (= U_{in\ max} * 0.8). \qquad (13)$$

The following equation results from the combination of equation (13) with equations (4a) and (4b):

$$I_{LED} = I_{LED\ max} * 0.8. \qquad (14)$$

This means that the rheostat 120 in the present example can cause a maximum reduction of the LED current, and therefore also of the LED power (since $U_{LED}$=constant), of only 20%. The brightness change thus achieved is hardly perceptible because of a brightness perception of the human eye which follows a power function (the perceived sensitivity of the brightness is proportional to the Stevens power function of the stimulation). The circuit is therefore not suitable in this form for replacing incandescent lamps with LED lamps.

The linear dimming characteristic of the LED 340, which is derivable from equation (14), is illustrated by the dashed brightness-voltage characteristic curve shown in FIGS. 7A and 7B having the designation "P_LED" and "P_LED_norm". The electrical power is again plotted as a measure of the brightness according to the rheostat deflection as a measure of the provided supply voltage (input voltage $U_{in}$ in FIG. 3). For better comparison of the LED characteristic curve to the incandescent lamp characteristic curve, reference is made to the normalized illustration in FIG. 7B. While the brightness of the incandescent lamp 160 has a quadratic dependence on the deflection of the rheostat 120, the LED 340 displays a linear dependence.

It can be stated that the virtual resistance of the LED lamps 300a, 300b is $(\eta/v_e)$-times higher (four times higher in the example described here) than the resistance of the incandescent lamp 160. The deflection of the rheostat 120 thus causes only a minor change in the input (and simultaneously dimming) voltage of the LED lamps. A further problem is that the reduction of the input (and dimming) voltage only reduces the LED current and not the LED voltage at the same time.

A method according to the invention for adjusting the brightness of at least one LED 340 according to a changing supply voltage provided by the supply apparatus 100 of the at least one LED 340 will now be described on the basis of FIG. 3, which voltage further improves the LED dimming described in conjunction with FIGS. 2B and 7. The method can be implemented by a control unit shown in FIGS. 4 to 6.

According to the method according to the invention, in a first step 510, a parameter is acquired, which indicates a changing supply voltage provided to the at least one LED 340. The acquired parameter can be a voltage value, which directly indicates the supply voltage provided by the electrical supply apparatus 100. Alternatively, the acquired parameter can also be a deflection value of the rheostat 120, which is proportional to the provided supply voltage.

For the direct acquisition of the supply voltage provided by the electrical supply apparatus 100, step 510 can comprise the following substeps. Coupling an electrical load resistor 408, which simulates an electrical resistance of the incandescent lamp 160, to the electrical supply apparatus 100; and acquiring the parameter by measuring the voltage which drops at the load resistor 408. In this case, the load resistor 408 simulating the incandescent lamp 160 has a resistance value which corresponds to the resistance value of the incandescent lamp 160 during operation. Therefore, the resistance of the incandescent lamp 160 in the circuit is simulated by means of the load resistor 408, wherein the voltage (or partial voltage) which drops at the load resistor 408 corresponds to the supply voltage provided to the incandescent lamp 160.

Depending on the acquired parameter, in a subsequent second step S20, a control voltage of the at least one LED 340 for adjusting an LED current is provided such that the at least one LED 340 has a predefined relative brightness change over a voltage range predefined by the supply apparatus 100. This can be similar or identical to a brightness change in an incandescent lamp 160. Alternatively, the control voltage can also be provided on the basis of the acquired parameter such that the at least one LED 340 has a brightness change (brightness characteristic curve) deviating from the incandescent lamp 160 over the predefined voltage range.

The predefined brightness change can be achieved by providing at least one predefined dimming characteristic curve. The predefined dimming characteristic curve describes a functional dependence of the control voltage on the acquired parameter for the predefined voltage range. This functional dependence can follow a predefined power function or logarithmic function. According to one variant, a quadratic dimming characteristic curve can be provided, which describes a quadratic change in the control voltage on the basis of the acquired parameter. A quadratic dimming characteristic similar to the dimming characteristic of the incandescent lamp 160 can thus be achieved.

According to a further variant, steps S10 and S20 can be repeated at short successive chronological intervals (for example, at intervals of a few milliseconds).

Further implementations of the method described here will be described in conjunction with the LED lamps illustrated in FIGS. 4 to 6.

Figure 4:
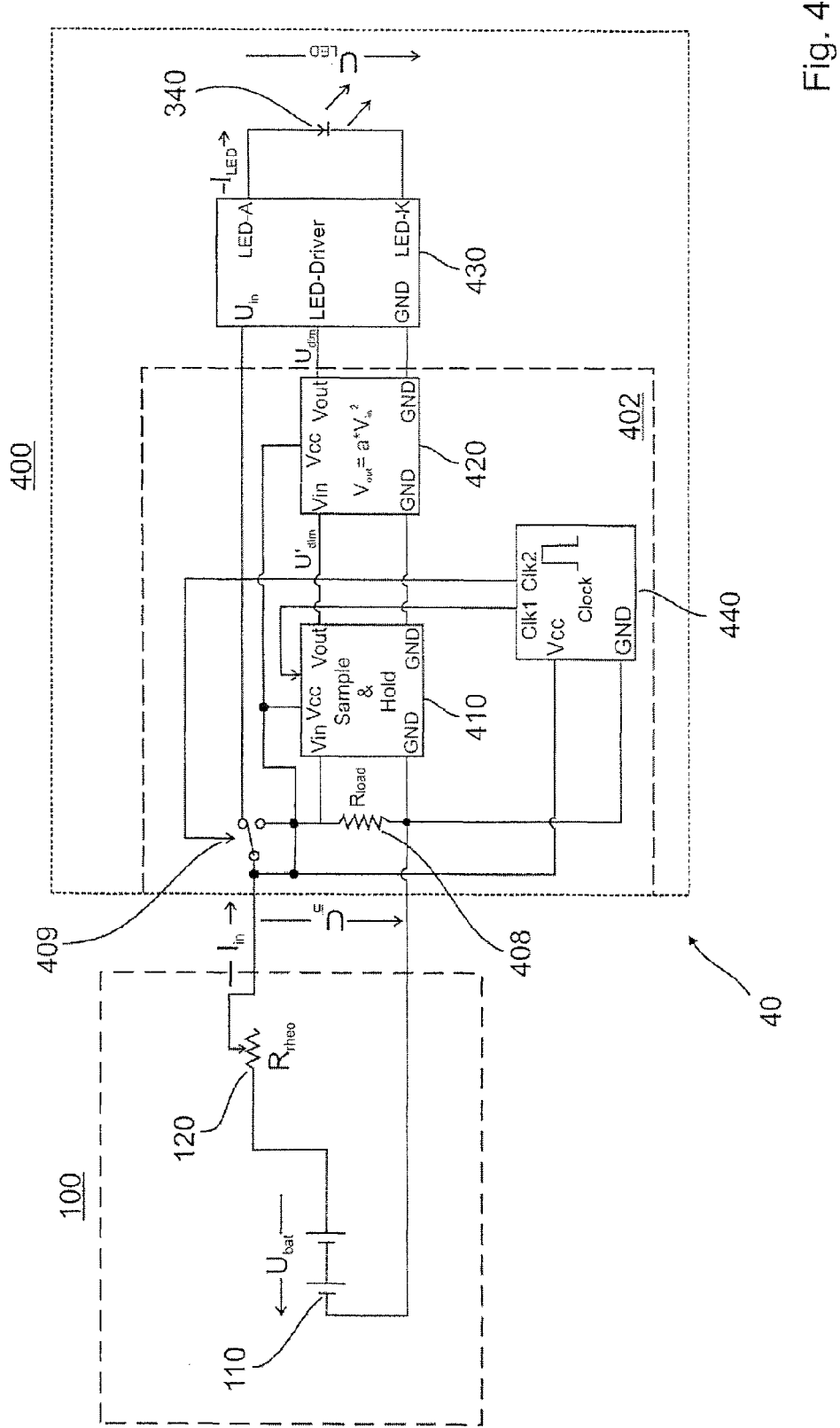
FIG. 4 shows a circuit diagram of a control unit for adjusting the brightness of an LED lamp according to one exemplary embodiment.

FIG. 4 shows the circuit diagram of a lighting apparatus 40. It comprises the electrical supply apparatus 100 having a voltage source 110 and rheostat 120, which was described in conjunction with FIG. 1. Furthermore, the lighting apparatus 40 comprises an LED lamp 400, which is electrically coupled to the supply apparatus 100. The LED lamp 400 can be designed such that it can be removably electrically coupled (not shown in FIG. 4) to the supply apparatus 100 via (two) electrical contacts. That is to say, the LED lamp 400 can be electrically coupled and decoupled to and from the supply apparatus 100 at any time.

The LED lamp 400 comprises at least one LED 340 (for generating a white light) and an LED driver 430 having a control input for dimming the LED light. The driver 430 can be a commercially available driver (as described above in conjunction with FIG. 2B) in this case. In contrast to the configuration shown in FIG. 2B, the LED lamp 400 comprises a further electrical control unit (shown by the dashed box 402 in FIG. 4), the output of which is electrically coupled to the LED driver 430. This control unit 402 comprises the load resistor 408, which is described above in conjunction with FIG. 3, an acquisition apparatus 410 (designated in FIG. 4 with "sample & hold"), a provision apparatus 420, a switching apparatus 409, and a clock generator apparatus 440, which is electrically coupled to the switching apparatus 409 and the acquisition apparatus 410. The acquisition apparatus 410, provision apparatus 420 and clock generator apparatus 440 are electrically coupled directly to the supply apparatus 100. The load resistor 408 and the LED driver 430 are electrically coupled to the supply apparatus 100 via the switching apparatus 409.

The clock generator apparatus 440 is designed to switch the switching apparatus 409 back-and-forth between a first switching state and a second switching state. For this purpose, the clock generator apparatus 440 generates an electrical pulse sequence, which consists of current pulses or voltage pulses. The pulse sequence can be generated in this case such that it repeats the current pulses or voltage pulses at a predefined frequency. The current pulses or voltage pulses can be generated, for example, at a frequency between 10 Hz and 10 000 Hz, preferably at a frequency between 100 Hz and 10 000 Hz. The switching apparatus 409 is accordingly switched back-and-forth between the two switching states at the set frequency.

In the first switching state, the switching apparatus 409 connects the electrical supply apparatus 100 to the load resistor 408, which has the resistance value $R_{load}$. A short time span is typically sufficient to acquire (measure) the voltage (partial voltage) $U'_{dim}$, which drops at the load resistor, according to a rheostat actuation. This can take a few microseconds. The dwell time of the switching apparatus 409 in the first switching state is accordingly substantially restricted to the required measurement time. The dwell time can be adjusted via the pulse duration of a pulse. After each measurement, the switching apparatus 409 is put back into the second switching state. In the second switching state, the switching apparatus 409 couples the LED driver 430 to the supply apparatus 100 for the electrical supply of the driver 430. It should be noted that the switching apparatus 409 predominantly remains in the second switching state and only decouples the LED driver 430 from the electrical supply apparatus 100 during the acquisition of the partial voltage U'$_{dim}$ which drops at the load resistor 408. As a result of the short dwell time in the first switching state, this has no significant effects on the driver supply and the driver control. This is because the LED driver 430 has at least one buffer capacitor for temporarily storing electrical power. This is sufficient to bridge the short interruptions.

Whenever the switch is switched in the first switching state, the partial voltage U'$_{dim}$ applied at the load resistor (this is dependent on the current rheostat deflection) can be measured. As a result of the high switching frequency, the measurement of the partial voltage U'$_{dim}$ which drops at the load resistor 408 can be repeated many times per unit of time (100 to 10 000 measurements per second are possible at the above-mentioned repetition rate frequency). Each chronological change in the partial voltage U'$_{dim}$ applied at the load resistor as a result of a rheostat actuation can be acquired "practically continuously". It is thus ensured that the brightness change to be adjusted is adapted to every resistance change at the rheostat 120 without noticeable delay.

The acquisition apparatus 410, which is coupled to the electrical load resistor 408, is provided for acquiring the partial voltage U'$_{dim}$ which drops at the load resistor. It acquires the potential difference applied at the electrical load resistor 408. The acquisition apparatus 410 is designed in the control unit 402 formed in FIG. 4 as an analog sample and hold circuit (frequently also referred to as an S/H circuit). The S/H circuit is designed to sample and briefly hold the partial voltage U'$_{dim}$ which drops at the load resistor 408. The sample and hold phases of the S/H circuit are in this case synchronized with the switching states of the switching apparatus 409. Specifically, the switching apparatus 409 and the S/H circuit are synchronized with one another such that the S/H circuit performs the sampling when the switching apparatus 409 is in the first switching state. In contrast, the S/H circuit is in the hold phase when the switching apparatus 409 is in the second switching state. For synchronization, the pulse sequence provided by the clock generator apparatus 440 is applied to the S/H circuit. According to one implementation, the pulse sequence (Clk1) provided to the S/H circuit can have a slight time delay in relation to the pulse sequence (Clk2) applied to the switching apparatus 409. It is thus ensured that the S/H circuit switches into the sample phase with a slight time delay in relation to the switching in the first switching state. By way of the slight time delay, settling effects in the circuit upon switching into the first switching state can be blanked out from the measurement.

In order that a similar dimming characteristic is achieved with the LED 340 as with the incandescent lamp 160 (see FIG. 7: quadratic dimming characteristic), the partial voltage U'$_{dim}$ acquired and provided by the acquisition apparatus 410 is processed further. This is performed by the provision apparatus 420, the input of which is electrically connected to the S/H circuit 410 and the output of which is connected to the control input of the LED driver 430.

The provision apparatus 420 is designed to convert the partial voltages U'$_{dim}$ provided by the S/H circuit 410 into control voltages U$_{dim}$. The provision apparatus 420 can comprise an electrical circuit for this purpose, which converts the provided partial voltages U'$_{dim}$ (as the input signal) into a control voltage U$_{dim}$ (as the output signal) according to the following equation:

$$U_{dim}=a*U'^2_{dim} \text{ with } a=U_{dim\ max}/(U_{bat})^2. \tag{15}$$

By means of equation (15) and the relationship $I_{LED}=I_{LED\ max}*(U_{dim}/U_{dim\ max})$ (see equation (4a) above), the following observation results:

$$I_{LED}=I_{LED\ max}*((a*U'^2_{dim})/U_{dim\ max}) \tag{16a}$$

$$I_{LED}=I_{LED\ max}*(((U_{dim\ max}/(U_{bat})^2)*U'^2_{dim})/U_{dim\ max}) \tag{16b}$$

$$I_{LED}=I_{LED\ max}*(U'_{dim}/U_{bat})^2. \tag{16c}$$

Since U'$_{dim\ max}$=U$_{bat}$, the following relationship follows:

$$I_{LED}=I_{LED\ max}*(U'_{dim}/U'_{dim\ max})^2. \tag{17}$$

The acquisition described here of the partial voltage U'$_{dim}$ which drops at the load resistor is repeated at an interval of, for example, several milliseconds. The brightness adjustment of the LED thus reacts very rapidly to the adjustment of the series resistance. In this case, the virtual resistance of the LED system does not play a role, since the voltage ratio which is predefined by the rheostat 120 is not ascertained at the input of the LED system, but rather briefly at the load resistor 408 (the resistance of which corresponds to the comparable incandescent lamp 160).

The following then applies for the electrical power of the LED according to the rheostat setting by means of the general relationship illustrated above in equation (3):

If the value R$_{rheo}$=0 is set at the rheostat, U$_{in}$=U$_{bat}$ and the following equations apply:

$$I_{LED}=I_{LED\ max} \tag{18a}$$

$$P_{LED}=U_{LED}*I_{LED}=U_{LED}*I_{LED\ max}=P_{LED\ max}\\(=v_e*P_{lamp\ max}) \tag{18b}$$

For example, if the rheostat is set to the value R$_{rheo}$=R$_{lamp}$=R$_{load}$, thus:

$$U'_{dim}=U'_{dim\ max}/2 \tag{19a}$$

$$I_{LED}=I_{LED\ max}*((U'_{dim\ max}/2)/U'_{dim\ max})^2=I_{LED\ max}/4 \tag{19b}$$

$$P_{LED}=U_{LED}*I_{LED}=U_{LED}*I_{LED\ max}/4=P_{LED\ max}/4 \tag{19c}$$

It can be seen from the equations (18a/b) and (19a-c) that a deflection of the rheostat 120 from the value 0 to the value R$_{lamp}$ causes the same relative power and therefore brightness change as in the incandescent lamp 120 (see equations (2a) and (2b)), namely from 100% to 25%. Of course, lower LED powers can also be set with a higher resistance value of the rheostat (R$_{rheo}$>>R$_{lamp}$).

In general, the following equivalent relationships apply for the LED power with the control voltage provided by the provision apparatus 420 (see equation 17):

$$P_{LED}=U_{LED}*I_{LED}=U_{LED}*I_{LED\ max}*(U'_{dim}/U'_{dim\ max})^2 \tag{20a}$$

$$P_{LED}=U_{LED}*I_{LED}=U_{LED}*I_{LED\ max}*(U_{in}/U_{in\ max})^2 \tag{20b}$$

$$P_{LED}=U_{LED}*I_{LED}=U_{LED}*I_{LED\ max}*(U_{in}/U_{bat})^2 \tag{20c}$$

$$P_{LED}=U_{LED}*I_{LED}=v_e*P_{lamp\ max}*(U_{in}/U_{bat})^2 \tag{20d}$$

$$P_{LED}=U_{LED}*I_{LED}=v_e*(U_{in}^2/R_{lamp}) \tag{20e}$$

It can be seen from equations (20a-e) that the dimming characteristic U$_{dim}$ of the LED lamp 400 obtained by the provided control voltage U$_{dim}$ corresponds to the dimming characteristic of the incandescent lamp 160 with a v$_e$-fold downscaling. The dimming characteristic obtained by the activation according to the invention of the LED lamp 400 is illustrated by the dotted curve "P_LED_new" in FIG. 7a. The normalized dimming characteristic is coincident with the normalized dimming characteristic of the incandescent lamp (P_Lamp_norm) in FIG. 7B and is therefore not visible.

The specified values are examples. The principle can also be applied to other rheostat resistances, η- and $v_e$.

The quadratic dimming characteristic curve ($V_0 = a^* V_{in}^2$) which is implemented in the provision apparatus 420 can alternatively also be formed as an interpolation, consisting of multiple linear characteristic curves.

Figure 3:
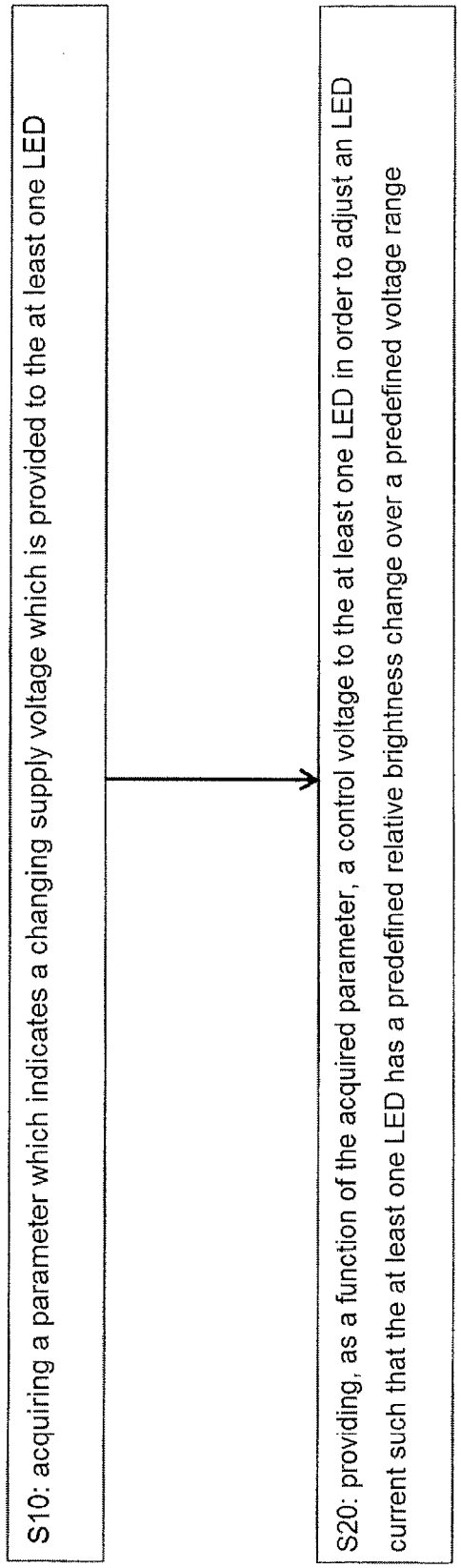
FIG. 3 shows a flow chart to illustrate a method according to the invention for adjusting the brightness of an LED lamp.
Figure 5:
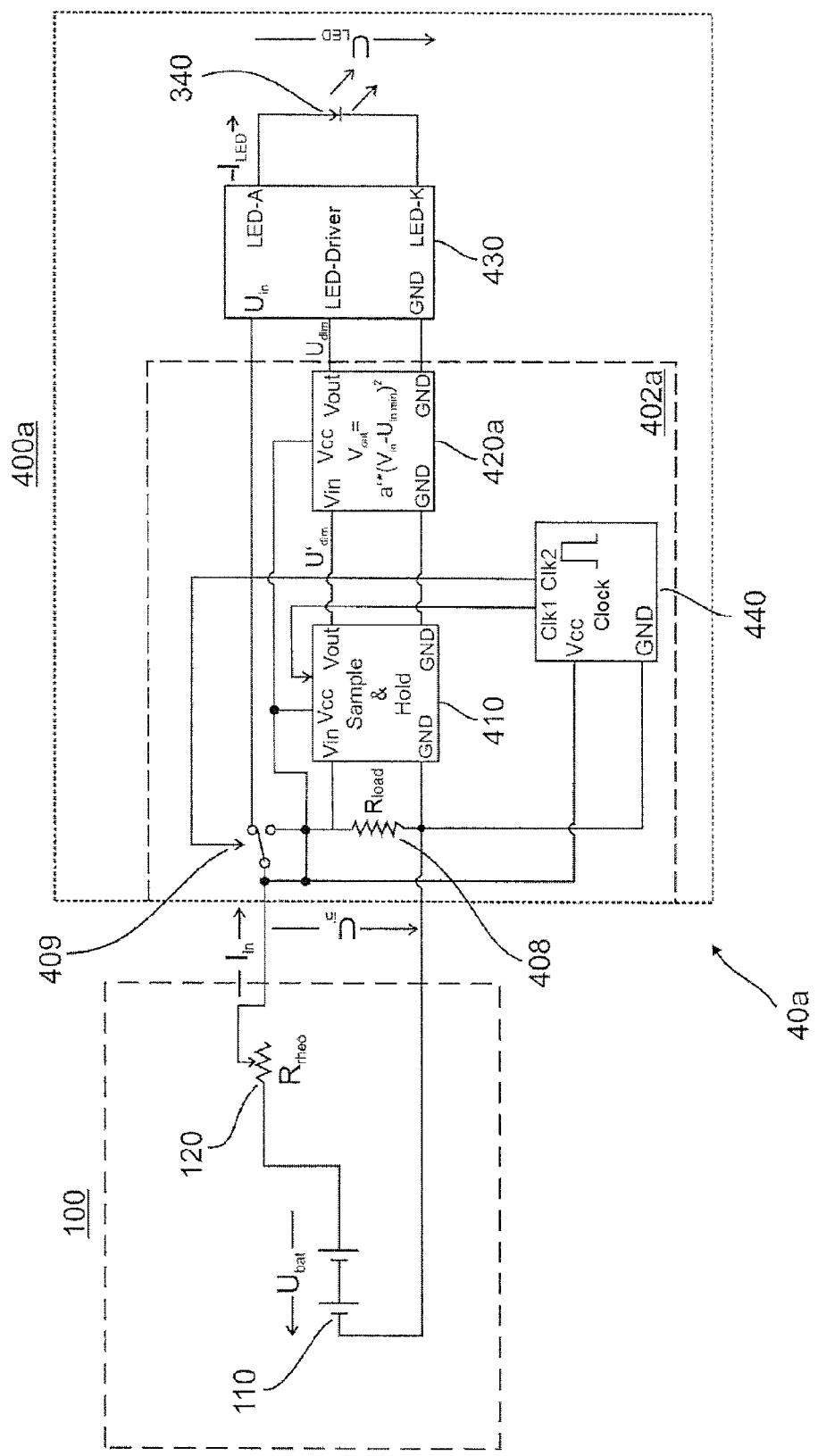
FIG. 5 shows a circuit diagram of a control unit for adjusting the brightness of an LED lamp according to a further exemplary embodiment.

A further circuit diagram of a lighting apparatus 40a having an LED lamp 400a is shown on the basis of FIG. 5, which comprises a control unit 402a according to the invention, which implements the method illustrated in conjunction with FIG. 3.

The circuit of the LED lamp 400a substantially corresponds to the circuit of the LED lamp 400 in FIG. 4. Reference is made in this regard to the description in conjunction with FIG. 4. The LED lamp 400a only differs on account of the embodiment of the provision apparatus 420a of the control unit 402a integrated in the LED lamp 400a.

As shown in FIG. 4 and FIG. 5, in addition to the LED driver 430, the acquisition apparatus 410, the provision apparatus 420, 420a and the clock generator apparatus 440 are coupled to the electrical supply apparatus 100 and are powered thereby. Depending on the voltage source used and in particular in the case of rheostats having higher resistance values ($R_{rheo}$), the input voltage $U_{in}$ at the LED lamp 400a can be adjusted to be sufficiently low that the electronic components of the control unit 402a (i.e. the acquisition apparatus 410, the provision apparatus 420, 420a and the clock generator apparatus 440) no longer function. To ensure the functionality of the electronic components, the input voltage $U_{in}$ cannot fall below a minimum voltage $U_{in\ min}$. However, this would have the result that arbitrarily low LED brightnesses cannot be set using the control unit 400a described here.

If the threshold value for the minimum input voltage is at $U_{in\ min}$ and a characteristic similar to an incandescent lamp is desired in the operating range between $U_{bat}$ and $U_{in\ min}$, such that slightly above $U_{in\ min}$ the brightness of the LED can be reduced to 0%, the control signal $U_{dim}$ at the control input of the LED driver 430 has to be modified further, specifically according to the following considerations.

If $U'_{dim} = U'_{dim\ max} = U_{bat}$, $U_{dim} = U_{dim\ max}$ should be reached (i.e. 100% of the LED brightness). In contrast, if $U'_{dim} = U_{in\ min}$, $U_{dim} = 0$ should be the case (i.e. 0% of the LED brightness).

Accordingly, the provision apparatus 420 shown in FIG. 4 is modified further such that it generates a control signal $U_{dim}$ and provides it to the LED driver 430, which converts the partial voltages $U_{dim}$ provided by the S/H circuit according to the following equation:

$$U_{dim} = a'^* (U'_{dim} - U_{in\ min})^2 \text{ with } a' = U_{dim\ max}/(U_{bat} - U_{in\ min})^2. \quad (21)$$

If the rheostat is adjusted to the value $R_{rheo} = 0$, $U'_{dim} = U_{bat}$ and it follows with equation 21:

$$U_{dim} = a'^* (U'_{dim} - U_{in\ min})^2 = (U_{dim\ max}/(U_{bat} - U_{in\ min})^2)^* (U_{bat} - U_{in\ min})^2 = U_{dim\ max}. \quad (22)$$

100% of the LED brightness is therefore reached at $R_{rheo} = 0$.

In contrast, if the rheostat is adjusted so that the minimum input voltage $U_{in} = U_{in\ min}$ is reached (i.e. at maximum rheostat actuation), the following thus applies:

$$U_{dim} = a'^* (U'_{dim} - U_{in\ min})^2 = (U_{dim\ max}/(U_{bat} - U_{in\ min})^2)^* (U_{in\ min} - U_{in\ min})^2 = 0. \quad (23)$$

0% of the LED brightness is therefore reached at $R_{rheo} = R_{rheo\ max}$.

The provision apparatus 420a therefore generates a control voltage which is offset-shifted by $U_{in\ min}$.

Figure 6:
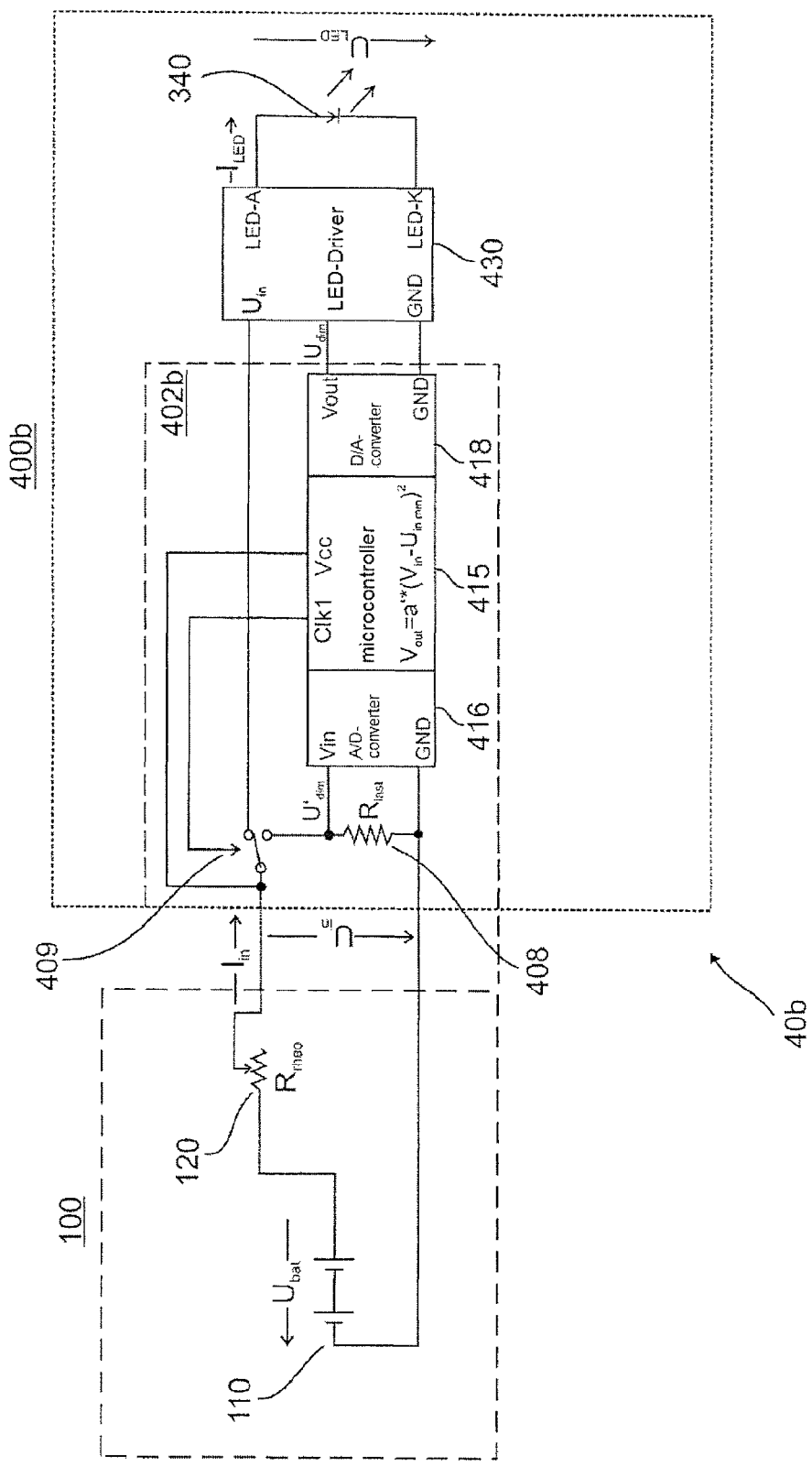
FIG. 6 shows a circuit diagram of a control unit for adjusting the brightness of an LED lamp according to a further exemplary embodiment.

A further circuit diagram of a lighting apparatus 40b having an LED lamp 400b is shown on the basis of FIG. 6, which lamp comprises a control unit 402b according to the invention, which implements the method described in conjunction with FIG. 3.

The LED lamp 400b differs from the LED lamps 400 and 400a shown in FIGS. 4 and 5 on account of the embodiment of the control unit 402. Instead of an analog S/H circuit 410 and provision apparatus 420, 420a, a microcontroller system 415 is now used, which performs both the clock generation and also the quadratic scaling (or scaling according to another power function or logarithmic function) of the acquired partial voltage $U'_{dim}$ which drops at the load resistor 408 and optionally the offset shift (by the value $U_{in\ min}$) described in conjunction with FIG. 5.

Furthermore, the control unit 402b comprises an A/D converter 416, which is designed to convert the partial voltage which drops at the load resistor 408 into a digital signal (bit sequence), and a D/A converter 418, which is designed to convert the digital control voltage signal provided by the microcontroller system 415 into an analog control voltage. The switching apparatus 409 and electrical load resistor 408 have the same arrangement and function within the control unit 402b as in the control units 400 and 400a of FIGS. 4 and 5. Reference is made in this regard to the corresponding description above.

By means of the technology described here LED lamps can be provided which have a similar power-voltage characteristic curve and accordingly a brightness-voltage characteristic curve like an incandescent lamp, but with only a fraction of the power consumption with equal light yield. The LED lamps can therefore be used to replace conventional incandescent lamps, without the electrical supply apparatuses having to be adapted for this purpose. This is particularly advantageous if electrical supply apparatuses are permanently installed in a device. This is frequently the case in medical diagnostic devices.

The invention claimed is:

1. A method for adjusting the brightness of at least one LED according to a changing supply voltage provided to the at least one LED, wherein the supply voltage is provided by means of an electrical supply apparatus, which is designed to provide supply voltages over a predefined voltage range to adjust the brightness of an incandescent lamp, wherein the method is carried out by means of a control unit, which is provided for electrically coupling the electrical supply apparatus (100) to the at least one LED, comprising the following steps:
   acquiring a parameter which indicates the changing supply voltage, wherein acquiring a parameter comprises selectively coupling and decoupling an electrical load resistor, which simulates an electrical resistance of the incandescent lamp, to and from the supply apparatus, and acquiring the parameter by measuring the voltage which drops at the load resistor; and
   providing, on the basis of the acquired parameter, a control voltage of the at least one LED for adjusting an LED current such that the at least one LED has a predefined relative brightness change over the predefined voltage range.

2. The method according to claim 1, wherein the step of providing a control voltage comprises:

calculating the control voltage on the basis of the acquired parameter and at least one predefined dimming characteristic curve, which, for the predefined voltage range, describes a dependence of the control voltage on the acquired parameter according to a predefined functional relationship.

3. The method according to claim 1, wherein the control voltage is provided such that a normalized brightness-voltage characteristic curve, which describes the relative brightness change, is substantially identical or similar to a normalized brightness-voltage characteristic curve of an incandescent lamp over the predefined voltage range.

4. The method according to claim 1, wherein the steps of acquiring a parameter and providing a control voltage are repeated at chronologically successive intervals.

5. The method according to claim 4, wherein the steps of acquiring a parameter and providing a control voltage are repeated at a predefined frequency.

6. A control unit for adjusting the brightness of at least one LED according to a changing supply voltage provided to the at least one LED, wherein the control unit is designed for electrically coupling the at least one LED to an electrical supply apparatus, which is designed to provide supply voltages over a predefined voltage range, to adjust the brightness of an incandescent lamp, comprising:
an electrical load resistor which is designed for simulating the electrical resistance of the incandescent lamp and provided for being selectively coupled to and decoupled from the electrical supply apparatus;
an acquisition apparatus which is designed to acquire a parameter which relates to the changing supply voltage, wherein the acquisition apparatus is designed to acquire the voltage which drops at the load resistor upon coupling of the electrical load resistor to the electrical supply apparatus and to provide said voltage to a provision apparatus as a parameter; and
the provision apparatus, which is designed to provide, on the basis of the acquired parameter, a control voltage of the at least one LED for adjusting an LED current such that the at least one LED has a predefined relative brightness change over the predefined voltage range.

7. The control unit according to claim 6, wherein the provision apparatus is designed to calculate the control voltage on the basis of the acquired parameter and at least one predefined dimming characteristic curve, which, for the predefined voltage range, describes a dependence of the control voltage on the acquired parameter according to a predefined functional relationship.

8. The control unit according to claim 6, further comprising:
a switching apparatus, which is designed to implement at least two switching states, wherein the switching apparatus electrically couples the load resistor to the electrical supply apparatus in a first switching state.

9. The control unit according to claim 8, further comprising a clock generator apparatus, which is electrically coupled to the switching apparatus and is designed to generate an electrical pulse sequence, in order to switch the switching apparatus back-and-forth between the at least two switching states.

10. The control unit according to claim 9, wherein the clock generator apparatus is designed to generate a pulse sequence having a predefined frequency.

11. The control unit according to claim 9, wherein the clock generator apparatus is furthermore electrically coupled to the acquisition apparatus and is designed to provide the generated pulse sequence to the acquisition apparatus for sampling the voltage which drops at the load resistor.

12. An LED lamp, which is designed for electrical coupling to an electrical supply apparatus, wherein the electrical supply apparatus is designed to provide supply voltages over a predefined voltage range, in order to adjust the brightness of an incandescent lamp, the LED lamp comprising:
A control unit, an IED driver which is electrically coupled to the control unit, and at least one LED, which is electrically coupled to the LED driver;
wherein the control unit is designed to provide a control voltage on the basis of the supply voltage provided by the electrical supply apparatus, and comprises:
an electrical load resistor which is designed for simulating the electrical resistance of the incandescent lamp and provided for being selectively coupled to and decoupled from the electrical supply apparatus;
an acquisition apparatus which is designed to acquire a parameter which relates to the changing supply voltage, wherein the acquisition apparatus is designed to acquire the voltage which drops at the load resistor upon coupling of the electrical load resistor to the electrical supply apparatus and to provide said voltage to a provision apparatus as a parameter; and
the provision apparatus, which is designed to provide, on the basis of the acquired parameter, a control voltage to the LED driver;
wherein the LED driver is designed to generate an LED current for the at least one LED on the basis of the provided control voltage such that the at least one LED has a predefined relative brightness change over the predefined voltage range; and
wherein the at least one LED is designed to generate a luminous flux on the basis of the provided LED current.

13. The LED lamp according to claim 12, wherein the LED lamp is provided for use in medical diagnostic devices.

14. An LED lighting apparatus, comprising:
an LED lamp; and
an electrical supply apparatus, which is coupled to the LED lamp and is designed to provide supply voltages over a predefined voltage range to continuously adjust the brightness of an incandescent lamp;
wherein the LED lamp comprises a control unit, an LED driver which is electrically coupled to the control unit, and at least one LED, which is electrically coupled to the LED driver;
wherein the control unit is designed to provide a control voltage on the basis of the supply voltage provided by the electrical supply apparatus, and comprises:
an electrical load resistor which is designed for simulating the electrical resistance of the incandescent lamp and provided for being selectively coupled to and decoupled from the electrical supply apparatus;
an acquisition apparatus which is designed to acquire a parameter which relates to the changing supply voltage, wherein the acquisition apparatus is designed to acquire the voltage which drops at the load resistor upon coupling of the electrical load resistor to the electrical supply apparatus and to provide said voltage to a provision apparatus as a parameter; and
the provision apparatus, which is designed to provide, on the basis of the acquired parameter, a control voltage to the LED driver;
wherein the LED driver is designed to generate an LED current for the at least one LED on the basis of the provided control voltage such that the at least one LED has a predefined relative brightness change over the predefined voltage range; and wherein the at least one LED is designed to generate a luminous flux on the basis of the provided LED current.

15. The LED lighting apparatus according to claim 14, wherein the supply apparatus comprises a fixed voltage source and a variable series resistor for adjusting the supply voltage in the predefined voltage range, wherein the load resistor can be coupled to the variable series resistor.

16. A medical diagnostic device, comprising an LED lighting apparatus according to claim 14.

* * * * *